US011993769B2

(12) United States Patent
Nguyen et al.

(10) Patent No.: US 11,993,769 B2
(45) Date of Patent: May 28, 2024

(54) COMPOSTABLE SILICA ENCAPSULATION OF OLIGONUCLEOTIDES FOR LONG-TERM STORAGE

(71) Applicant: MICROSOFT TECHNOLOGY LICENSING, LLC, Redmond, WA (US)

(72) Inventors: Bichlien Hoang Nguyen, Seattle, WA (US); Karin Strauss, Seattle, WA (US); Robert Grass, Zurich (CH); Jan Wendelin Stark, Langenthal (CH); Julian Bernhard Koch, Zurich (CH)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 342 days.

(21) Appl. No.: 17/230,849

(22) Filed: Apr. 14, 2021

(65) Prior Publication Data
US 2022/0333095 A1 Oct. 20, 2022

(51) Int. Cl.
*C12N 15/10* (2006.01)
(52) U.S. Cl.
CPC .................. *C12N 15/1006* (2013.01)
(58) Field of Classification Search
None
See application file for complete search history.

(56) References Cited

U.S. PATENT DOCUMENTS 5,663,358 A 9/1997 Cohen et al.
2019/0388862 A1 12/2019 Strauss et al.

FOREIGN PATENT DOCUMENTS

EP 2644703 A1 10/2013

OTHER PUBLICATIONS

Chen, et al., "Combining Data Longevity with High Storage Capacity—Layer-by-Layer DNA Encapsulated in Magnetic Nanoparticles", In Journal of Advanced Functional Materials, vol. 29, Issue 28, Jul. 2019, 8 Pages.
Church, et al., "Next-Generation Digital Information Storage in DNA", In Journal of Science, vol. 337, Issue 6102, Aug. 16, 2012, 2 Pages.

(Continued)

*Primary Examiner* — Alexandre F Ferre
(74) *Attorney, Agent, or Firm* — Benjamin Keim; Newport IP, LLC

(57) ABSTRACT

This disclosure describes particles and techniques for storing oligonucleotides that provide stable, long-term protection yet are also compostable. A core is coated with a layer of oligonucleotides and encapsulated under an outer layer of non-porous, hydrolyzed organosilicon disulfide. The hydrolyzed organosilicon disulfide protects the oligonucleotides from oxidative and thermal damage under typical storage conditions. One suitable organosilicon disulfide is bis(3-triethoxysilylpropyl) disulfide (BTSPD). The oligonucleotides may be retrieved by contacting the particles with a reducing agent that degrades the disulfide bonds in the outer layer. The disulfide bonds enable removal of the protective encapsulation without the use of dangerous chemicals such as hydrogen fluoride. Instead of retrieving the oligonucleotides, the particles may be disposed of in a composting environment. In an implementation, the oligonucleotides are artificially synthesized and encode digital information.

20 Claims, 9 Drawing Sheets

(56) References Cited

OTHER PUBLICATIONS

Croissant, et al., "Biodegradable Ethylene-Bis(Propyl)Disulfide-Based Periodic Mesoporous Organosilica Nanorods and Nanospheres for Efficient In-Vitro Drug Delivery", In Journal of Advanced Materials, vol. 26, Issue 35, Sep. 2014, 7 Pages.

Dimopoulou, et al., "Storing Digital Data Into DNA: A Comparative Study of Quaternary Code Construction", In Proceedings of the IEEE International Conference on Acoustics, Speech and Signal Processing, May 4, 2020, pp. 4332-4336.

Du, et al., "Disulfide-Bridged Organosilica Frameworks: Designed, Synthesis, Redox-Triggered Biodegradation, and Nanobiomedical Applications", In Journal of Advanced Functional Materials, vol. 28, Issue 26, Jun. 2018, 35 Pages.

Graf, et al., "A General Method to Coat Colloidal Particles with Silica", In Journal of Langmuir, vol. 19, Issue 17, Aug. 19, 2003, pp. 6693-6700.

Grass, et al., "Covalently Functionalized Cobalt Nanoparticles as a Platform for Magnetic Separations in Organic Synthesis", In Angewandte Chemie International Edition, vol. 46, Issue 26, Jun. 25, 2007, pp. 4909-4912.

Nghiem, et al., "Oxidation Reduction Potential as a Parameter to Regulate Micro-Oxygen Injection into Anaerobic Digester for Reducing Hydrogen Sulphide Concentration in Biogas", In Journal of Bioresource Technology, vol. 173, Dec. 1, 2014, pp. 443-447.

Organick, et al., "Probing the Physical Limits of Reliable DNA Data Retrieval", In Journal of Nature Communications, vol. 11, Issue 1, Jan. 30, 2020, 7 Pages.

Organick, et al., "Random Access in Large-Scale DNA Data Storage", In Journal of Nature Biotechnology, vol. 36, Issue 3, Mar. 2018, pp. 242-248.

Paunescu, et al., "Reversible DNA Encapsulation in Silica to Produce ROS-Resistant and Heat-Resistant Synthetic DNA Fossils", In Journal of Nature Protocols, vol. 8, Issue 12, Nov. 7, 2013, pp. 2440-2448.

Reddy, et al., "Effect of Alternate Aerobic and Anaerobic Conditions on Redox Potential, Organic Matter Decomposition and Nitrogen Loss in a Flooded Soil", In Journal of Soil Biology and Biochemistry, vol. 7, Issue 2, Mar. 1, 1975, pp. 87-94.

Remond, et al., "Silicon-Containing Amino Acids: Synthetic Aspects, Conformational Studies, and Applications to Bioactive Peptides", In Journal of Chemical Reviews, vol. 116, Issue 19, Oct. 12, 2016, pp. 11654-11684.

Takahashi, et al., "Demonstration of End-to-End Automation of DNA Data Storage", In Scientific Reports, vol. 9, Issue 1, Mar. 21, 2019, 5 Pages.

Kamegawa, et al., "Functionalization of silica nanoparticles for nucleic acid delivery", In Journal of Nano Research, vol. 11, Issue 10, Jun. 27, 2018, pp. 5219-5239.

Mikutis, et al., "Silica-Encapsulated DNA-Based Tracers for Aquifer Characterization", In Journal of Environmental Science & Technology, vol. 52, Issue 21, Oct. 2, 2018, pp. 12142-12152.

Paunescu, et al., "Detecting and Number Counting of Single Engineered Nanoparticles by Digital Particle Polymerase Chain Reaction", In Journal of ACS Nano, vol. 9, Issue 10, Aug. 10, 2015, pp. 9564-9572.

"International Search Report and Written Opinion Issued in PCT Application No. PCT/US22/023182", dated Jul. 15, 2022, 9 Pages.

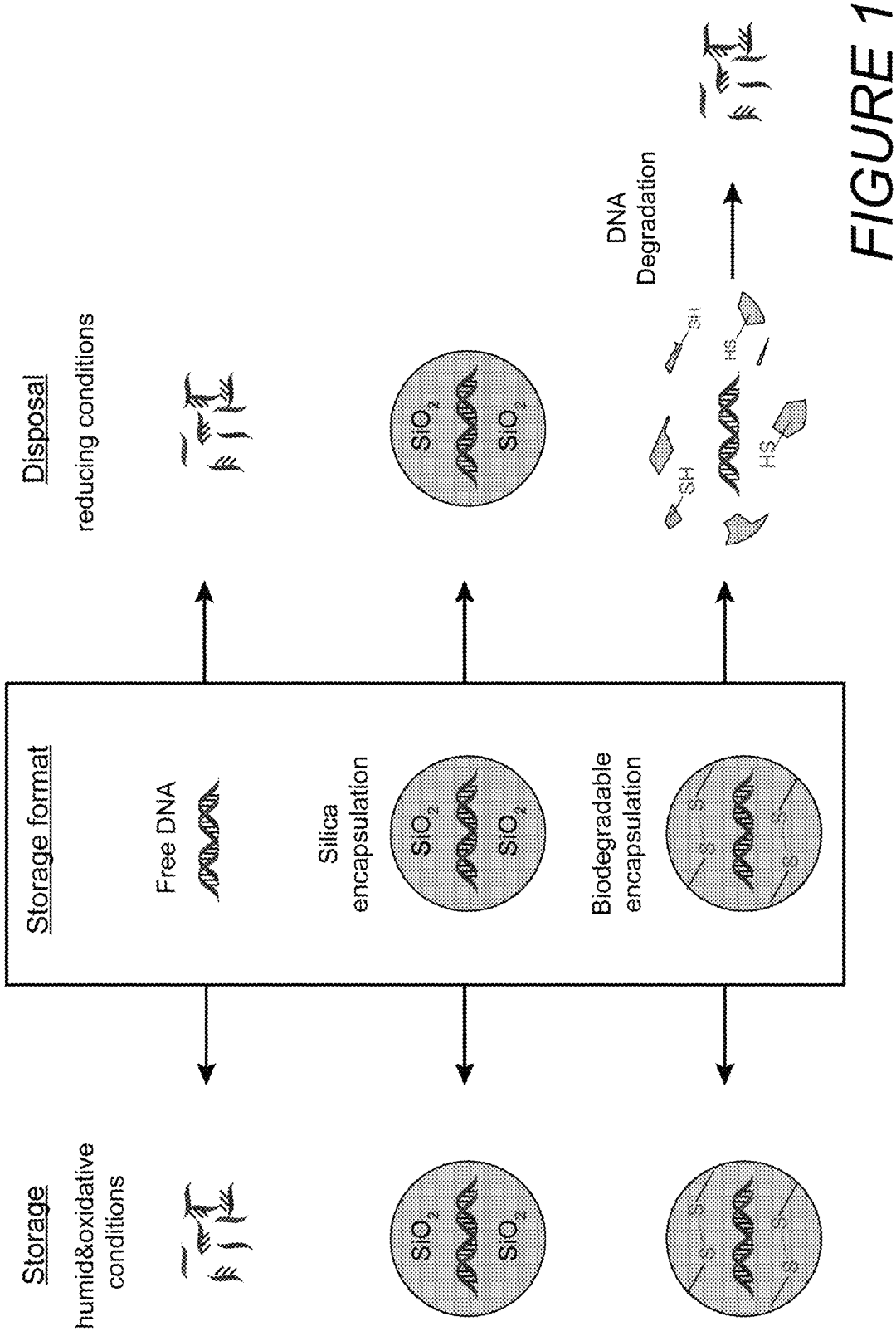

GSH 8 mM
Day 0            Day 30
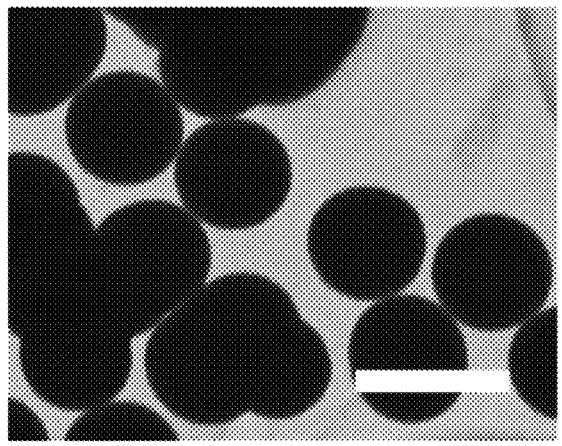 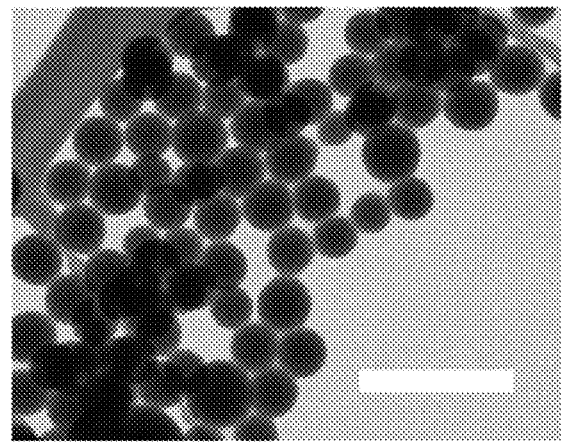
*FIGURE 7A*
in water            +TCEP
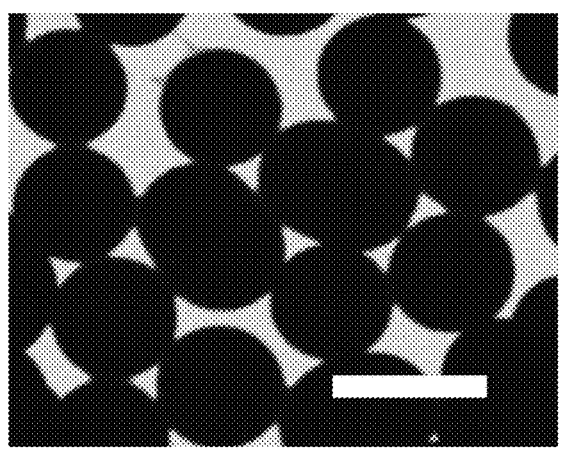 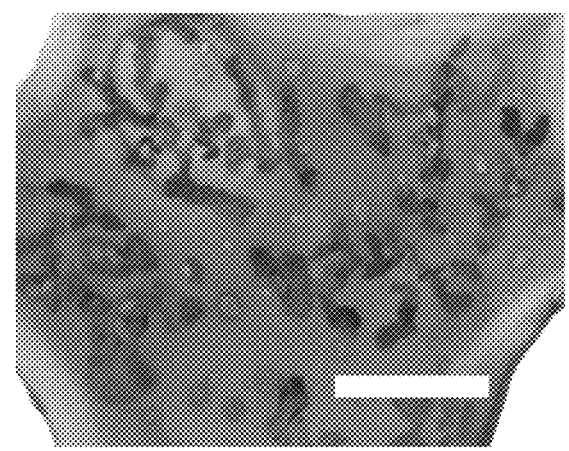
*FIGURE 7B*

COMPOSTABLE SILICA ENCAPSULATION OF OLIGONUCLEOTIDES FOR LONG-TERM STORAGE

BACKGROUND

The amount of digital data produced worldwide is drastically increasing and new technologies with higher storage densities and storage lifetimes are required to keep up with the demand. Research has shown the potential for use of oligonucleotides such as deoxyribonucleic acid (DNA) in digital data storage applications (Church et al. 2012, Science; Organick et al. 2018, Nat. Biotech.). As a storage medium, oligonucleotides have several advantages over conventional media. Oligonucleotides have a much higher theoretical data density than existing technologies, potentially storing 250 Exabytes (i.e., 250 billion Gigabytes) per gram of DNA (Organick et al. 2020, Nat. Comm.). In addition, magnetic or optical storage technologies have a lifetime of five to 10 years, while properly stored DNA has a predicted lifetime of hundreds or thousands of years based on the recovery of intact DNA from fossils. Finally, data storage using oligonucleotides has much lower energy demand compared to current server farms that use electronic media to store data.

Storage conditions have a substantial effect on the long-term stability of oligonucleotides. Oligonucleotides are organic molecules and therefore susceptible to degradation by chemical and radiative damage. When stored in solution, DNA is stable for approximately 10 years which is the same timescale as other storage media. However, state-of-the-art DNA stabilization methods achieve long shelf life estimated to be as much as hundreds or thousands of years.

One technique for long-term storage encapsulates oligonucleotides in glass (Sift) for data storage purposes. Paunescu et al. 2013, Nat. Prot., describes a method for encapsulating DNA into amorphous silica (glass) spheres, mimicking the protection of nucleic acids within ancient fossils. A silica surface layer is grown onto the DNA by the poly-condensation of tetraethoxysilane (TEOS; sol-gel process). Similar encapsulation techniques using silica are described in EP 2,644,703A1 and US 2019/0388862A1.

These existing techniques provide a high level of protection but require a toxic and dangerous etching solution to remove the silica and access the encapsulated DNA. Also, oligonucleotides encapsulated in silica may persist in the environment unless intentionally destroyed leading to possible breaches of data security. This disclosure addresses these and other considerations.

SUMMARY

This disclosure is directed to structures and techniques that protect oligonucleotides by encapsulation in biodegradable particles. The structures and processes of this disclosure provide stable, long-term storage for oligonucleotides under conventional storage conditions. Yet the oligonucleotides can be retrieved from storage without dangerous chemicals and the stored oligonucleotides are degraded in biological environments allowing the destruction of encoded data by composting.

This disclosure introduces a biodegradable encapsulation technology, using dithiol-linked glass monomers. Dithiol-linked glass monomers are organosilicon disulfide compounds that degrade under reducing conditions found in biological environments (Croissant et al. 2014, Mater. Views). Particle cores are functionalized and coated with a layer of oligonucleotides that may encode digital data. An interacting layer is created over the adsorbed oligonucleotides and then encapsulated by a sol-gel process with an organosilicon disulfide precursor. This technique creates particles that contain a layer of oligonucleotides between a core and outer shell of hydrolyzed organosilicon disulfide.

The encapsulation protects oligonucleotides against oxidative and thermal damage to provide long shelf-life. However, when exposed to reducing conditions, as encountered in some biological environments such as anoxic composting, the coating disintegrates through disulfide bond reduction, exposing the oligonucleotides to degradation through enzymes and hydrolysis.

This coating strategy allows for long-term data storage at ambient conditions (e.g., 20° C. and 50% relative humidity) but can also be broken down in reducing environments. Thus, the particles are a compostable yet stable storage technology. The same property allows for the de-encapsulation of oligonucleotides without the hydrogen fluoride etching solution used to remove silica. Less toxic reducing agents such as Tris(2-carboxyethyl)phosphine (TCEP) can be used to reduce the disulfide bonds in the compostable coating and release the oligonucleotides. Relative to silica encapsulation, the particles of this disclosure provide environmental and worker safety benefits by eliminating the need to use toxic hydrogen fluoride etching solutions to access or destroy the oligonucleotides. It also provides a further environmental benefit because data stored in oligonucleotides may be deleted naturally through composting of the particles. Composting can be performed without the use of chemical reagents and with minimal energy inputs.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to structure(s), system(s), and/or method(s) as permitted by the context described above and throughout this document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

FIG. 1 is a diagram illustrating different storage formats and disposal conditions for storage of DNA.

4c is a STEM image of the cores coated with a DNA layer and encapsulated in an outer layer of hydrolyzed BTSPD. Scale bar is 500 nm.

Figure 5:
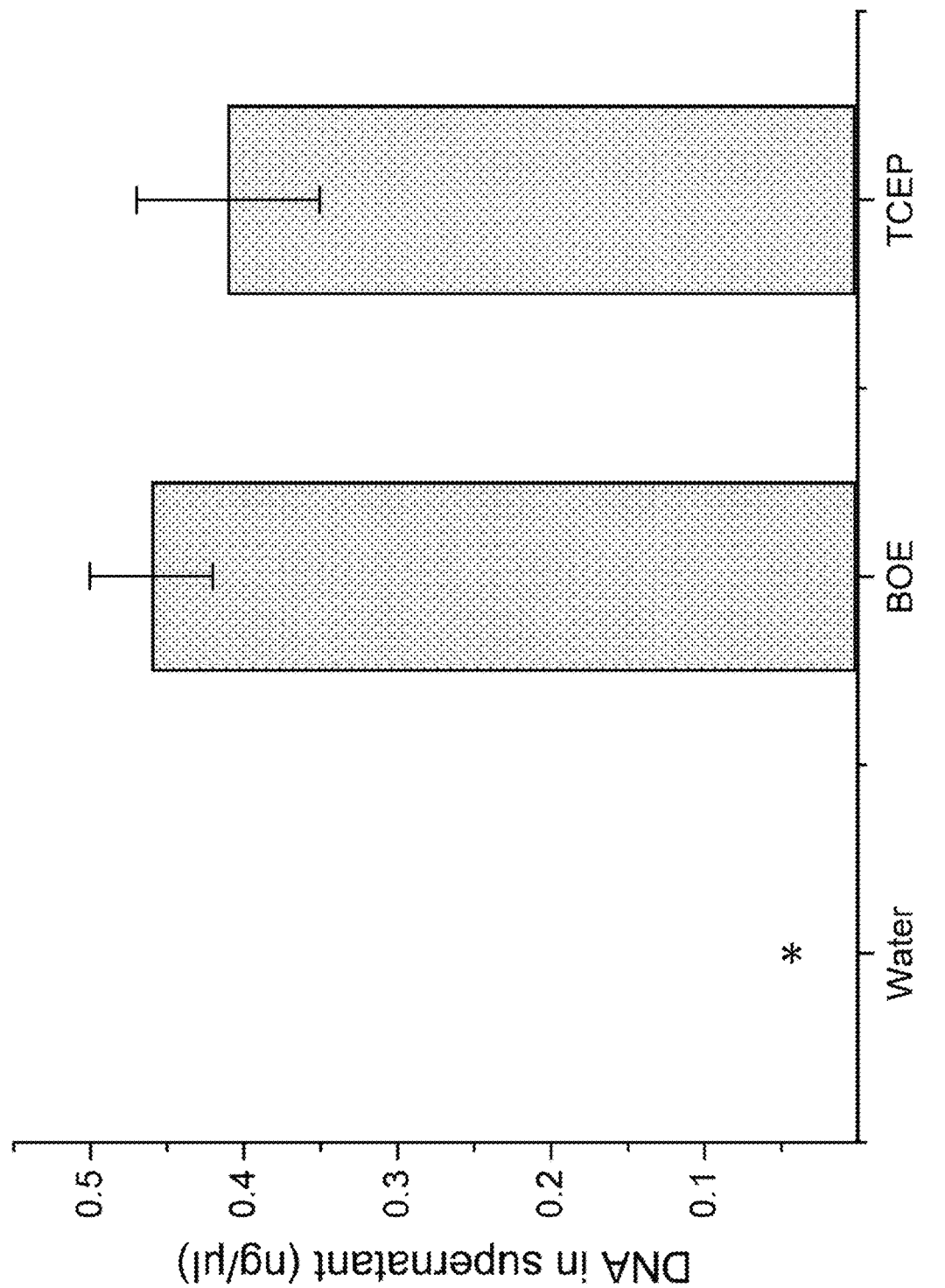

FIG. 5 shows the amount of DNA recovered from particles produced according to the techniques of the disclosure when released using buffered oxide etch (BOE) and TCEP.

FIG. 6 shows a) the amount of DNA remaining after incubation in bleach solution for 10 minutes and b) loss of DNA due to accelerated aging at 60° C. and 50% relative humidity.

FIG. 7 shows STEM images of the degradation of particles when a) exposed to 8 mM glutathione (GSH) at 37° C. and b) when exposed to 0.2 M TCEP. Scale bar is 500 nm.

Figure 8:
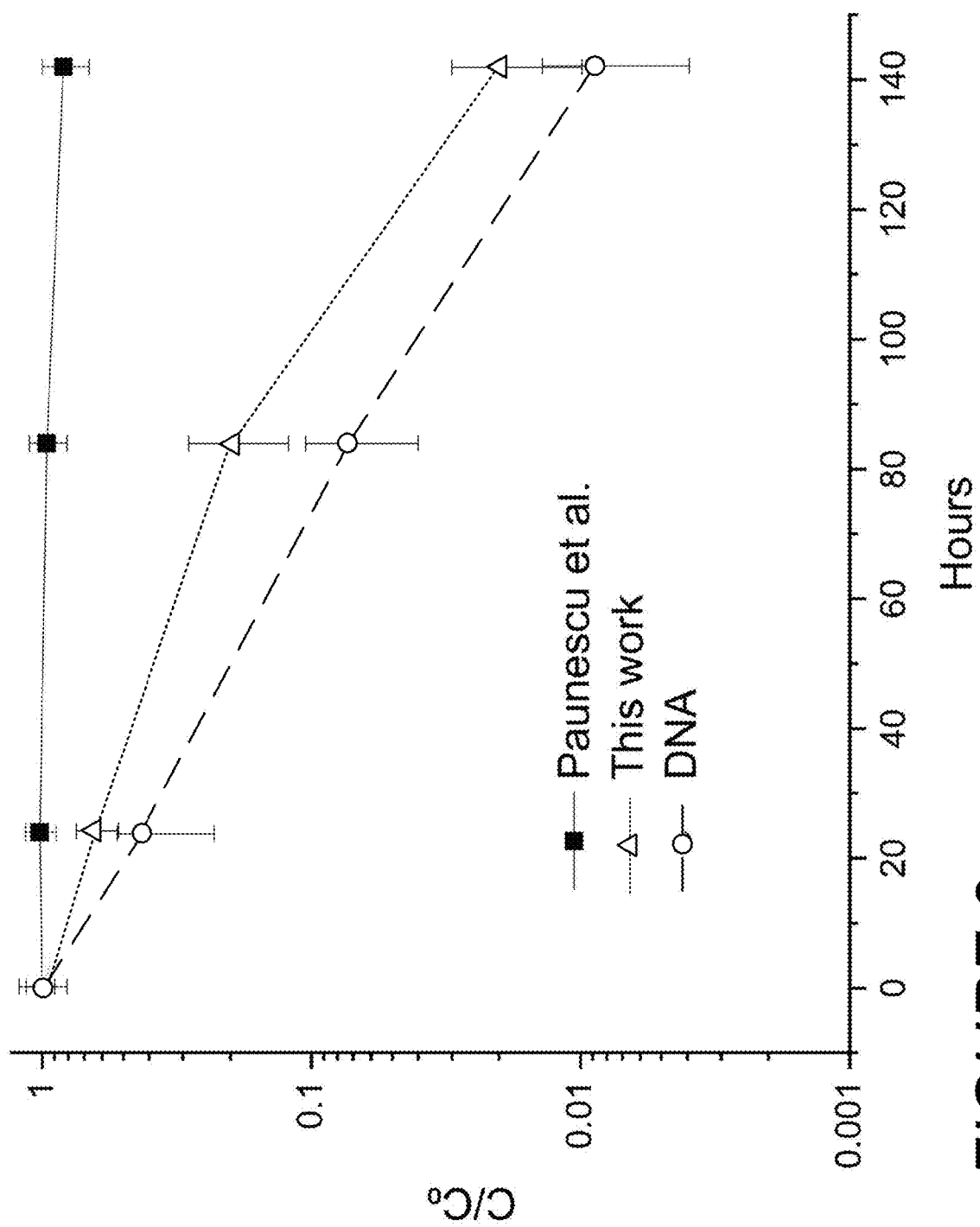

FIG. 8 shows loss of DNA under composting conditions.

DETAILED DESCRIPTION

FIG. 1 compares the effect of storage format on DNA stability under conventional storage conditions and reducing conditions. Conventional storage conditions are about 20° C. (e.g., 15-25° C.) and about 50% (e.g., 30-70%) relative humidity with exposure to atmospheric oxygen. The reducing conditions used for disposal are created by contact with a chemical reducing agent or exposure to a composting environment.

Free DNA (e.g., double-stranded ~150 bp), such as in an aqueous solution, is not protected by encapsulation and degrades in conventional storage conditions within weeks or months. Free DNA can be disposed of readily in reducing conditions. Although disposal is convenient, free DNA is not a suitable storage format for long-term storage because the DNA degrades under conventional storage conditions.

Silica encapsulation, such as described in Paunescu et al. protects the DNA from degradation under conventional storage conditions. However, $SiO_2$ resists degradation under reducing conditions. Toxic chemicals such as a hydrogen fluoride etching solution must be used to remove the encapsulation. If particles containing silica-encapsulated DNA are disposed of in the garbage or placed outside in the environment, the DNA will not readily degrade. The particles themselves will persist in the environment and become waste that needs to be managed. Even if disposed of properly, there is a possibility the particles may be retrieved, the DNA accessed, and any encoded digital data recovered. However, when disposing of data stored in DNA, it is desirable to provide certainty that the data is deleted.

Biodegradable encapsulation with an organosilicon disulfide, the subject of this disclosure, provides both stability under conventional storage conditions and ease of disposal in reducing conditions. Disulfide bonds in hydrolyzed organosilicon disulfide are reduced to two thiol groups breaking the covalent sulfur-sulfur bonds and dissolving the protective encapsulation. The DNA is released and may be purified, amplified, and sequenced to retrieve any encoded data. Alternatively, once released from protection, the DNA may be degraded and any encoded data becomes unrecoverable.

The contents of the disclosure may be used with any type of oligonucleotide. References to DNA are merely illustrative of one type of oligonucleotide and not intended to limit the application to only DNA. Oligonucleotide as used herein refers to both single- and double-stranded DNA and ribonucleic acid (RNA) including polynucleotides that have unnatural or non-canonical bases and DNA-RNA hybrids. These structures and techniques described in this disclosure have applications for storing synthetic oligonucleotides encoding digital information but are equally suitable for storing naturally occurring oligonucleotides.

Figure 2A:
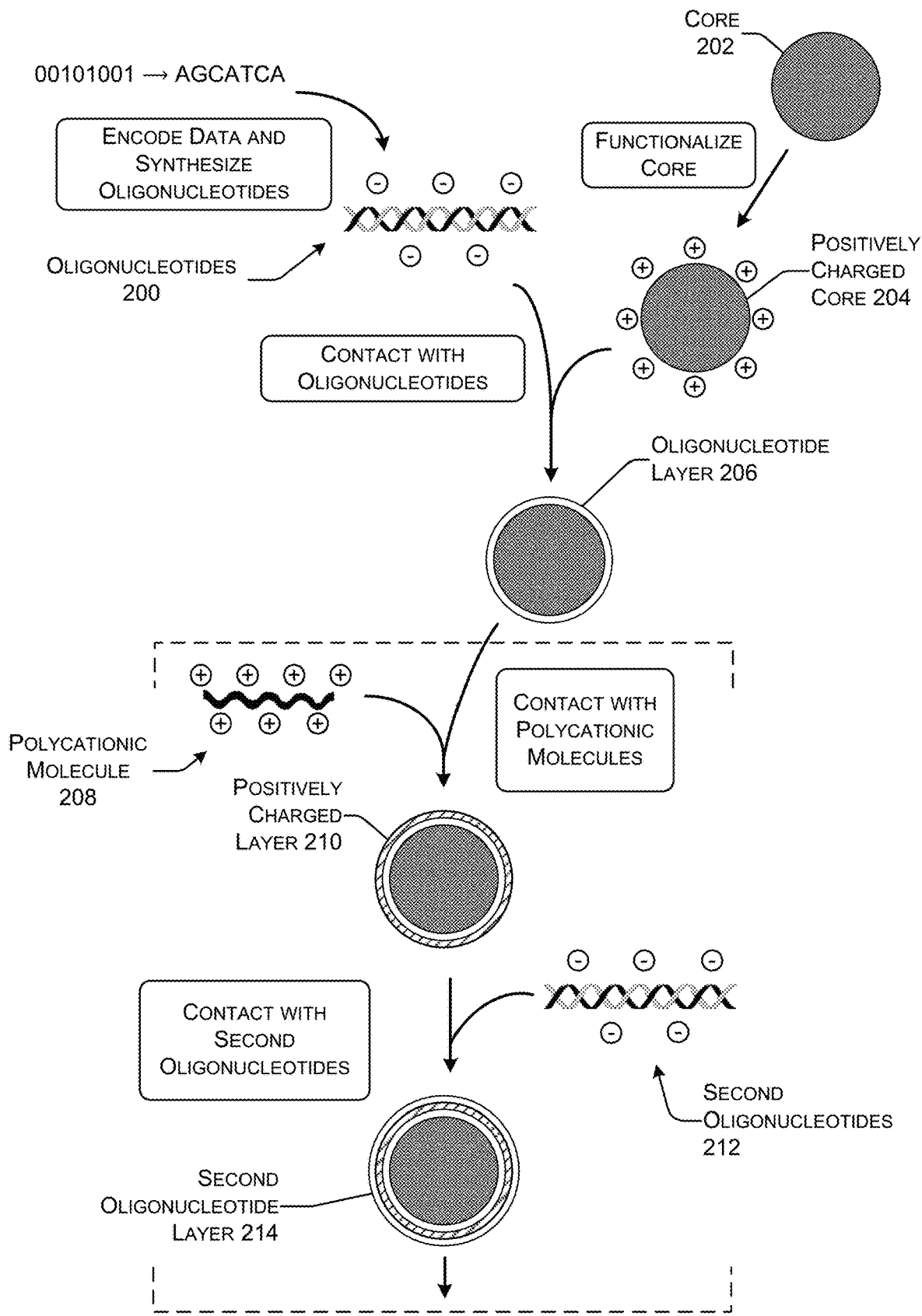
FIGS. 2a and 2b show schematic steps of a process for creating particles containing oligonucleotides encapsulated in a hydrolyzed organosilicon disulfide. The process shows the release of the oligonucleotides from the particles or breakdown of the particles by composting.
Figure 2B:
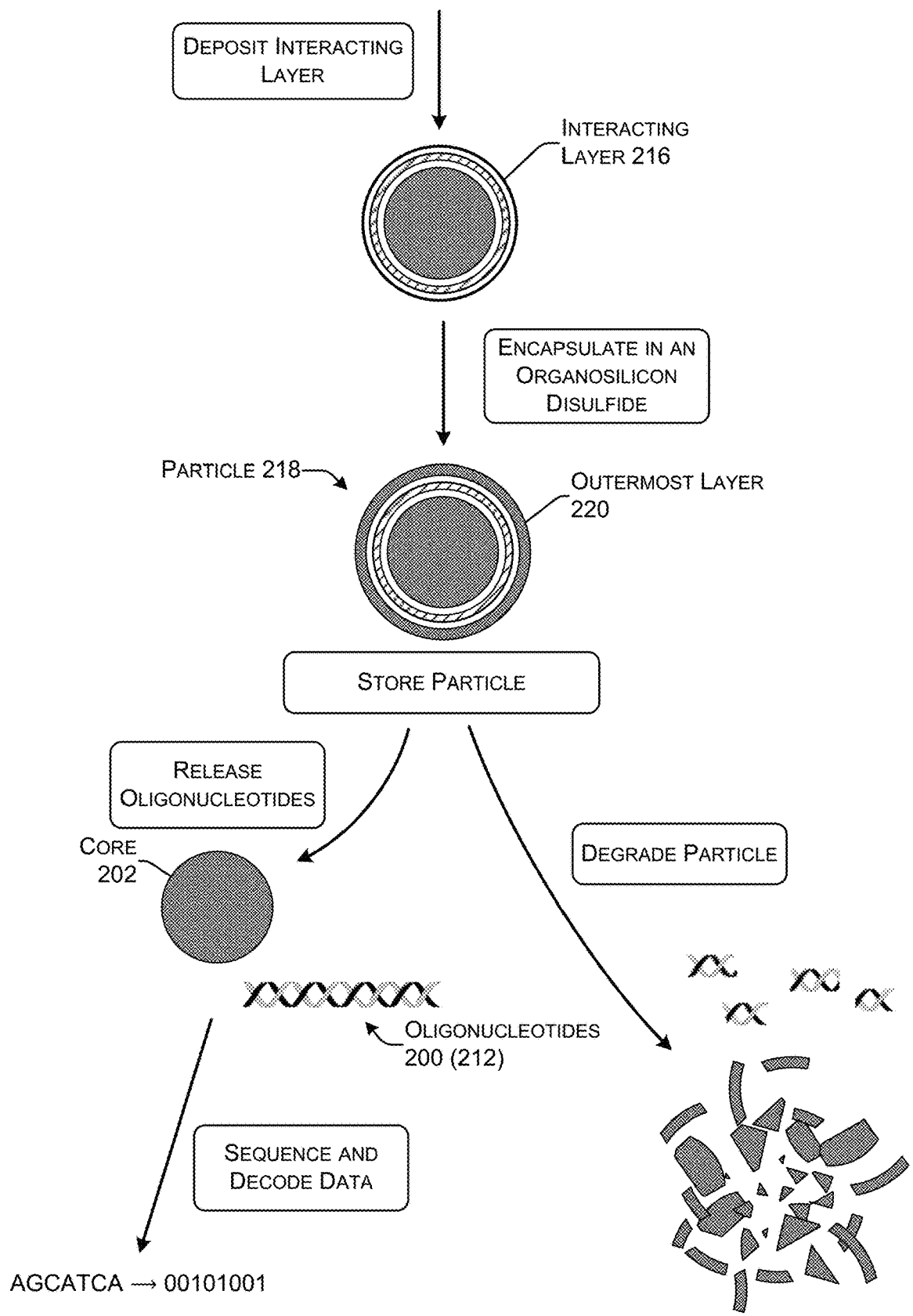

FIGS. 2a and 2b show a schematic process that stores oligonucleotides encoding data on the particles of this disclosure followed by retrieval of the oligonucleotides or disposal of the particles and the oligonucleotides.

Digital data is encoded in a sequence of nucleotide bases and corresponding oligonucleotides 200 are synthesized. Techniques for encoding data in oligonucleotides and synthesizing oligonucleotides with arbitrary sequences are known in the art (Organick et al.; Takahashi et al. 2019, Nature; WO 2013/178801 A2). The oligonucleotides 200 may encode digital data such as all or a portion of a computer file using any encoding scheme currently existing or later developed.

The oligonucleotides 200 may be synthesized by the phosphoramidite method, enzymatic synthesis, or any later-developed technique for creating oligonucleotides with arbitrary sequences. In various implementations, the oligonucleotides 200 may be single- and double-stranded DNA and ribonucleic acid (RNA) including polynucleotides that have unnatural or non-canonical bases and DNA-RNA hybrids. The oligonucleotides 200 may be any length. For example, a length of the oligonucleotides 200 may be approximately 80-300 base pairs (bp), approximately 100-200 bp, approximately 120-180 bp, or approximately 150 bp. The oligonucleotides 200 may be provided in an aqueous solution such as a buffer at a concentration of, for example, around 20, 30, 40, 50, 60, 70, 80, 90, or 100 µg/mL.

A core 202 provides a substrate for the oligonucleotides 200. The core 202 may be spherical but is not limited to spherical shapes and may be oblong or otherwise non-spherical. The core 202 may be a nanoparticle or nanosphere. Nanoparticle or nanosphere as used herein refers to a structure with a diameter or longest dimension of less than one micron (1000 nm). In various implementations, the core 202 may have a diameter of between about 100-500 nm, about 200-400 nm, about 100 nm, about 150 nm, about 300 nm, about 300 nm, about 350 nm, about 400 nm, about 450 nm, or about 500 nm.

The core 202 may be made from any material that can be coated with oligonucleotides 200. For example, the core 202 may comprise silica, mesoporous silica, a hydrolyzed organosilicon disulfide (e.g., formed from a disulfide tri-ethoxysilane precursor such as BTSPD), a plastic, a nonmetallic material, or a metal. The term "silica" is known as the chemical compound $SiO_2$ in both its crystalline and amorphous state. Silica also includes amorphous glass matrices with a Sift content of at least 70 wt %. Glass matrices may include other elements such as, but not limited to, carbon, sodium, calcium, boron, lead, titanium, phosphorous, and aluminum. As used herein, silica and mesoporous silica do not contain disulfide bonds. In contrast, organosilicon disulfides include sulfur-sulfur bonds.

Examples of metal cores include iron, cobalt, nickel, and alloys thereof. Examples of nonmetallic cores include iron oxide, cobalt oxide, and nickel oxide. Techniques for creating nanoparticles out of these materials are known to those of ordinary skill in the art. The core may be magnetic such as "TurboBeads" available from TurboBeads LLC (Zurich, Switzerland; Grass et al. 2007, Angew. Chem. Int. Ed.).

In an implementation, a commercially available product may be used as the core 202. For example, the core 202 may be a silica sphere (e.g., monodisperse 200 nm, 300 nm, or 500 nm). As a further example, the core 202 may be a TurboBead. The core 202 may also be created by any suitable technique. For example, core 202 may be formed with a sol-gel process from a tetra alkoxysilane such as tetramethyl orthosilicate, tetraethyl orthosilicate (TEOS), tetrapropyl orthosilicate, tetrabutyl orthosilicate, tetrapentyl orthosilicate, or mixtures thereof. TEOS easily converts to silicon dioxide upon the addition of water. This hydrolysis reaction is an example of a sol-gel process. The side product is ethanol. The reaction proceeds via a series of condensation reactions that convert the TEOS molecule into a mineral-like solid via the formation of Si—O—Si linkages. Rates of this conversion are sensitive to the presence of acids and bases, both of which serve as catalysts.

The core 202 may be formed from hydrolysis of organosilicon disulfide compounds. Organosilicon disulfide compounds include disulfide triethoxysilanes one example of which is BTSPD. Representative organosilicon disulfide compounds and methods of making the same are known to those of ordinary skill in the art and described in U.S. Pat. No. 5,663,358. Examples of biodegradable silica-based materials including organosilicon disulfide compounds are also described in Du et al. 2018, Adv. Funct. Matter. A hydrolyzed organosilicon disulfide core may be formed by a sol-gel process from organosilicon disulfide precursors. Cores may be formed from bis(triethoxysilyl)ethylene or bis(3-triethoxysilylpropyl)disulfide using the techniques described in Croissant, et al. Hydrolyzed organosilicon disulfide cores formed by the techniques of Croissant, et al., that blend bis(triethoxysilyl)ethylene and BTSPD will be porous. However, a core formed from BTSPD alone using the techniques of Croissant, et al. will be non-porous. A core is considered porous if it contains open pores accessible from (or in communication with) the external surface of the core and the pores have a volume of greater than about 0.1 $cm^3/g$ as determined by nitrogen absorption. A core is considered non-porous if the volume of such pores is less than about 0.1 $cm^3/g$ or preferably less than about 0.01 $cm^3/g$. The core 202 may be porous or non-porous depending on the material and technique for forming the core 202. The core 202 may also be solid or hollow.

In an implementation, non-porous organosilicon disulfide cores may be formed by combining water, ethanol (e.g., 99.8% EtOH) and a strong base (e.g., NaOH) with stirring followed by addition of cetyltrimethylammonium bromide (CTAB) micellar template. The mixture may be heated (e.g., to around 80° C.) and stirred (e.g., 50 min at about 1000 rpm). An organosilicon disulfide precursor is added (e.g., BTSPD) The stirring speed may be increased to about 1400 rpm. Stirring at an elevated temperature may be continued (e.g., around 80° C. for about 2 h). The mixture can then be cooled to room temperature and cores extracted using a solution of ammonium nitrate in ethanol with sonication (e.g., 30 min at 50° C.) and centrifugation (e.g., 15 min at 8000 g). The cores may then be washed multiple times with ethanol then with water and finally redispersed in water.

The core 202 is functionalized to create a positively charged core 204. "Functionalization" as used herein means the introduction of functional groups to a surface. The functional groups may be selected in part based on their charge. Functionalization may add any type of functional group to the core 202 that imparts a positive surface charge. The positive surface potential may be, for example, about +10 to 40 mV, about +15 to 30 mV, or about +25 mV. Functionalization may be achieved by known chemical processes based on the composition of core 202 and the functional group to be added.

In an implementation, the core 202 is functionalized by contacting the core 202 with a amino silane to functionalize the surface of the core 202 with amine groups. Amine groups include primary amines (—$NH_2$), secondary amines (—NHR), tertiary amines (—$NR_1R_2$), and quarternary amines (—$N^+R_1R_2R_3$). The amino silane may be, but is not limited to, a quaternary amine having a silyl moiety such as the hydrolysis products of N-trimethoxysilylpropyl-N,N,N-trimethylammonium chloride (TMAPS) or amino propyl triethoxysilane (APTES). Techniques for functionalizing silica with TMAPS are described in Paunescu et al. In one implementation, the core 202 may be functionalized by adding TMAPS to cores in isopropanol (e.g., iPrOH, >99.5%) dispersed by sonication. The mixture may be stirred (e.g., 900 rpm for 12 h) and then centrifuged (e.g., 3 min at 21,500 g). The supernatant can be removed and the particles resuspended in isopropanol. Techniques for functionalizing silica with APTES are described in EP 2644703 A1. Other techniques for functionalizing silica or glass to impart a positive surface charge are known to those of ordinary skill in the art. Surface functionality created by any of the above techniques gives the core 202 a positive charge making a positively charged core 204.

The core 202 is then contacted with a solution containing the oligonucleotides 200, which are strongly negatively charged due to the phosphate groups on the backbone. The term "contacting" refers to any suitable way of contacting one substance with another as described herein in the context of building layers on nanoparticles. Thus, "contacting" includes a simple addition as well as intense mixing. The solution may be any solution suitable for the storage of oligonucleotides such as water or a buffer. For example, the oligonucleotides 200 may be in a solution of annealing buffer (e.g., at a concentration of 50 µg/ml). The annealing buffer may be any standard buffering solution for oligonucleotides such as 400 mM Tris-HCl, 500 mM NaCl, and 100 mM $MgCl_2$.

The oligonucleotides 200 adsorb strongly on the surface of the positively charged core 204. Adsorption is the adhesion of atoms, ions or molecules from a gas, liquid or dissolved solid to a surface. This process creates a film of the adsorbate on the surface of the adsorbent. The addition of the oligonucleotides 200 may be followed by vortexing and ultrasonification. Although ultrasonification can fragment genomic DNA, oligonucleotides several hundreds of bases in length are not damaged by ultrasonification. Contacting the positively charged core 204 with the oligonucleotides 200 creates an oligonucleotide layer 206 adsorbed to the positively charged core 204.

In an implementation, the oligonucleotides 200 in water are combined with a solution containing the positively charged cores 204 with vortexing followed by shaking. The shaking may be performed at about 400-600 rpm such as at about 400 rpm, 500 rpm, or 600 rpm. The shaking may be performed for about 15-25 minutes such as for about 15, 16, 17, 18, 19, 20, 21, 22, 23, 24, or 25 minutes. Following shaking, the mixture may be centrifuged (e.g., 3 min 21,000 rpm) and the supernatant removed.

Multiple layers of oligonucleotides alternating with layers of polycationic molecules 208 may be added to the surface of the core 202. This optional portion of the process is indicated by dashed brackets in FIG. 2a. Oligonucleotide density may be increased by creating multiple layers of oligonucleotides 200 on the core 202. The oligonucleotides in the oligonucleotide layer 206 are contacted with polycationic molecules 208. The polycationic molecules 208 may be diluted in water (e.g., to a concentration of 2.6 mg/mL). The addition of the polycationic molecule 208 may be performed by vortexing the core 202 with the polycationic molecules 208 followed by ultrasonification. This results in the core 202 having a positively charged layer 210 of the polycationic molecule 208 adsorbed to the oligonucleotide layer 206. The polycationic molecules 208 in the positively charged layer 210 may then be contacted with second oligonucleotides 212. The second oligonucleotides 212 adsorb to the positively charged layer 210 forming a second oligonucleotide layer 214 separated from the oligonucleotides 200 by the polycationic molecules 208. Without being bound by theory, it is believed that the alternating positive and negative charges of the layers create a stable structure through electrostatic forces.

In an implementation, a solution of polycationic molecules 208 may be added to the microcentrifuge tube containing the cores 202, vortexed, and then ultrasonicated for approximately 30 seconds. The cores 202 may be separated from the supernatant. The cores 202 may then be washed by addition of water, brief vortexing, and ultrasonification for 10 seconds. Following this wash, a solution containing the second oligonucleotides 212 may be added to the microcentrifuge tube, vortexed, and placed in the ultrasonic bath for 30 seconds. During this time the some or all of the second oligonucleotides 212 are adsorbed to the positively charged layer 210. The supernatant, which potentially contains oligonucleotides, may be collected and reused.

These steps may be repeated to create multiple oligonucleotides layers 206, 214 alternating with positively charged layers 210. In implementations, two, three, four, five, six, or more oligonucleotide layers may be formed. Multiple layers of oligonucleotides increase the quantity of oligonucleotides that can be stored per unit of volume or weight as compared to a particle having only a single oligonucleotide layer 206. Repeating these steps multiple times involves repeatedly separating particles from a supernatant. Thus, if the core 202 is magnetic, a magnetic separator may be used to facilitate the separation. If the core 202 is not magnetic, other techniques such as filtering and drying may be used to separate the cores with oligonucleotide layers from the supernatant.

As used herein, "polycationic molecule" 208 means a molecule that has three or more separate sites which could potentially be positively charged. The polycationic molecule 208 may be a polycationic linear macromolecule such as polyethyleneimine (PEI), poly-1-lysine (PLL), diethylaminoethyl-dextran (DEAE-dextran), or a branched polymer such as poly(amidoamine) (PAMAM) dendrimers. PEI or polyaziridine is a polymer with the repeating unit composed of the amine group and two-carbon aliphatic $CH_2CH_2$ spacer. Linear polyethyleneimines contain all secondary amines. PLL is a specific chiral configuration of the synthetic polymer α-polylysine with L-lysine at lysine's central carbon. DEAE-dextran is a positively charged dextran derivative that binds and interacts with negatively-charged oligonucleotides and via an unknown mechanism. PAMAM, is a class of dendrimer that is made of repetitively branched subunits of amide and amine functionality. PAMAMs have a sphere-like shape overall and are typified by an internal molecular architecture including tree-like branching, with each outward 'layer,' or generation, containing exponentially more branching points. Surface amine residues on PAMAM dendrimers bind to the phosphate backbone of DNA through charged interactions.

FIG. 2b continues the process from FIG. 2a and shows depositing an interacting layer 216. The interacting layer 216 provides a coating over the oligonucleotide layer 206, 214 to provide a substrate for growth of an organosilicon disulfide hydrolysis product. Without being bound by theory, it is believed that the interacting layer 216 adsorbs to the oligonucleotide layer 206, 214 electrostatically. The interacting layer 216 may be formed from an amphiphilic, nonionic polymer.

In an implementation, the interacting layer 216 comprises polyvinylpyrrolidone (PVP). PVP, also commonly called polyvidone or povidone, is a water-soluble polymer made from the monomer N-vinylpyrrolidone. Depositing the interacting layer 216 may cause PVP to be adsorbed to the oligonucleotide layer 206, 214. Thus, the interacting layer 216 may be created by contacting the core 202 with PVP. In various implementations, an average molar mass of the PVP may be, but is not limited to, 3.5 kg/mol (PVP-3.5), 10 kg/mol (PVP-10), 40 kg/mol (PVP-40), or a different molar mass.

Contacting the core 202 with PVP may include adding PVP (e.g., 750 µl, 45 g/l) to a suspension of cores followed by vortexing and shaking (e.g., 800 rpm). Shaking may be continued for 12-36 hours, such as for 20, 21, 22, 23, 24, 25, 26, 27, or 28 hours. After shaking, the mixture of PVP and cores may be centrifuged (e.g., 100 rpm for 45 min). One technique for coating colloids with PVP and then silica is described in Graf et al. 2003, Langmuir.

Following formation of the interacting layer 216, the core 202 and adsorbed oligonucleotides 200 are encapsulated in a hydrolyzed organosilicon disulfide to form a particle 218 with an outermost layer 220 of non-porous organosilicon disulfide hydrolysis product. Hydrolyzed organosilicon disulfide is not limited to any single chemical formula but refers to glassy, solid, colloidal reaction products formed by the hydrolysis and polymerization of ethoxylated or methoxylated organosilicon compounds. The particle 218 may contain a single oligonucleotide layer 206 or, if layers of oligonucleotides are alternated with layers of positively charged molecules, multiple oligonucleotide layers (e.g., 2, 3, 4, 5, 6, or more oligonucleotide layers).

In an implementation, the outermost layer 220 may comprise the hydrolysis product of a disulfide triethoxysilane. In an implementation, the disulfide triethoxysilane is BTSPD. In an implementation, both the core 202 and the outermost layer 220 may be formed of the same material. For example, the core 202 and the outermost layer 220 may both comprise the hydrolysis product of a non-porous organosilicon disulfide. For example, the core 202 and the outermost layer 220 may both comprise the hydrolysis product of a disulfide triethoxysilane. As an additional example, the core 202 and the outermost layer 220 may both comprise the hydrolysis product of BTSPD. In an implementation, the core 202 and the outermost layer 220 may be formed from different materials. For example, the core 202 may be silica and the outermost layer 220 may be a non-porous organosilicon disulfide such as hydrolyzed BTSPD or the core 202 may be the hydrolysis product of a porous organosilicon disulfide and the outermost layer 220 may be the hydrolysis product of a non-porous organosilicon disulfide.

In an implementation, encapsulating the core 202 in organosilicon disulfide comprises adding the organosilicon disulfide to the core 202 while shaking in a solution of ammonia in ethanol (e.g., 4.2% $NH_3$ in EtOH) for at least about 20, 21, 22, 23, 24, 25, 26, 27, or 28 hours. Thus, the outermost layer 220 may be formed following formation of the interacting layer 216 by resuspending the cores 202 in $NH_3$/EtOH with vortexing followed by shaking (e.g., 900 rpm) before the addition of an organosilicon disulfide. Without being bound by theory, it is believed that the ammonia catalyzes the sol-gel reaction of the organosilicon disulfide. For example, 1 µl of BTSPD may be added to 1 ml of $NH_3$/EtOH containing the cores 202. Shaking may be maintained for a prolonged time such as one day, two days, three days, four days, five days, or longer. A greater quantity of BTSPD may increase the thickness of the outermost layer 220. Following contacting with the organosilicon disulfide, the suspension may be centrifuged (e.g., 3 min at 15,000 g) and the supernatant removed. The particles 218 formed by addition of the outermost layer 220 may be washed with ultrapure water and stored in the water. The particles 218 may also be dried (e.g., air dry, lyophilization, vacuum centrifuge with decanting, heating, etc.) and then stored as dry particles.

Once the oligonucleotides 200 are encapsulated in hydrolyzed organosilicon disulfide, the particle 218 may be stored indefinitely. The particle 218 may be stored in the vessel used to create it (e.g., a centrifuge tube such as Falcon® tubes available from Fisher Scientific) or transferred to another vessel for storage. Storage conditions may be selected to further enhance the longevity of the oligonucleotides 200. For example, the oligonucleotides 200 in the particles may be stored at cool temperatures with low humidity such as, for example, 9° C. and 20% relative humidity. When encased in hydrolyzed organosilicon disulfide and stored under favorable conditions, the oligonucleotides 200 may be preserved without significant degradation for hundreds, thousands, or potentially millions of years.

Following storage, the particle 218 may be processed to release the oligonucleotides 200 encased within. For example, if digital data encoded by the oligonucleotides 200 is desired, the particle 218 that contains the oligonucleotides 200 encoding that data may be located and the outermost layer 220 removed. Alternatively, if the oligonucleotides 200 are no longer needed, for example if a user wishes to delete the digital data encoded in the oligonucleotides 200, the particle 218 may be degraded to destroy both the particle 218 itself and the encapsulated oligonucleotides 200.

Following storage, the oligonucleotides 200 may be released from organosilicon disulfide encapsulation by contacting the particle 218 with a reducing agent that dissolves the outermost layer 220 without harming the oligonucleotides 200. The reducing agent reduces the disulfide bonds in the hydrolyzed organosilicon disulfide to two thiol groups causing the organosilicon disulfide to degrade. If the core 202 is also formed of hydrolyzed organosilicon disulfide it will degrade as well. In implementations, the reducing agent may be TCEP or GSH.

For example, the particles 218 may be suspended in TCEP (e.g., 0.02M) which rapidly dissolves organosilicon disulfides. As a further example, the particles 218 may be suspended in GSH (e.g., 8 mM at pH 7.2) for 30 days. Although reducing agents may be preferable because they are typically not toxic or dangerous to handle, a hydrogen fluoride solution may also be used to remove the hydrolyzed organosilicon disulfide encapsulation. Hydrogen fluoride solutions commonly used to degrade silica will also degrade hydrolyzed organosilicon disulfides. Silica and hydrolyzed organosilicon disulfides dissolve rapidly in fluoride-containing solutions (forming $SiF_6^{2-}$). Thus, a buffered oxide etch (BOE) containing fluoride may be used to dissolve the outermost layer 220. The compatibility of dilute etching solutions and oligonucleotides (DNA is not affected by $F^-$ ions) has previously been shown. The hydrogen fluoride solution may be a mixture of a buffering agent such as ammonium fluoride ($NH_4F$) and hydrofluoric acid (HF). In an implementation, BOE may be prepared by dissolving ammonium hydrogen difluoride ($NH_4FHF$) in $H_2O$ and dissolving $NH_4F$ in $H_2O$ then mixing the two solutions together. The vapors of buffered hydrogen fluoride solutions can penetrate skin and rapidly damage cells and bones.

Once released from encapsulation, the oligonucleotides 200 may be purified to remove remnants of the organosilicon disulfide, salts, and other compounds from the solution leaving "clean" oligonucleotides that are ready for further processing. Multiple techniques for purifying samples containing oligonucleotides are known to those of ordinary skill in the art such as dialysis and purification columns. If a hydrogen fluoride solution such as BOE is used to remove the organosilicon disulfide, a first step of the purification may be adjusting the pH to neutral (e.g., 6-8) such as by addition of potassium phosphate buffer (0.5 M, pH 7). Suitable techniques for purifying oligonucleotides 200 following removal of an outermost layer 220 with a hydrogen fluoride solution are described in US Pat. App. No. 2019/0388862 A1.

The solution of dissolved organosilicon disulfide and oligonucleotides 200 may be purified by adding a buffer and placing the solution into a purification column followed by centrifugation. There are many commercially available purification kits suitable for oligonucleotide purification. For example, the QIAquick PCR purification kit (Qiagen, cat. no. 28104) may be used to purify the oligonucleotides 200.

If the particle 218 contains multiple oligonucleotide layers 206, 214 separated by one or more positively charged layers 210, the purification may include separating the oligonucleotides 200, 212 from the polycationic molecules 208. The solution following degradation of the hydrolyzed organosilicon disulfide may be combined with a release solution that contains polyanionic molecules which displace the oligonucleotides 200, 212 from the polycationic molecules 208. The release solution may be made by diluting 40 mg of poly(acrylic acid) sodium (PAS) in 50 mL of ultrapure water to a concentration of 0.8 mg/mL and mixing that with sodium chloride diluted in ultrapure water until saturation at room temperature in a ratio of PAS:NaCl=20:80. PAS is a polyanionic molecule that displaces the oligonucleotides from polycationic molecules 208 such as PEI. Addition of the release solution may be followed by vortexing and ultrasonification (e.g., 30 s).

Once the oligonucleotides 200 are released from encapsulation and sufficiently purified, the oligonucleotides 200 may be sequenced. Following recovery, and before sequencing, the oligonucleotides 200 may be amplified. The oligonucleotides 200 may be amplified by polymerase chain reaction (PCR) which increases the amount of oligonucleotides available for sequencing or other processing. Sequencing may be performed by any known or later developed technique that reads the sequence of bases in an oligonucleotide and generates sequence information representing the order of the bases. Suitable sequencing techniques include, but are not limited to, nanopore sequencing (Oxford Nanopore Technologies) or sequencing by synthesis (Illumina). If the oligonucleotides 200 encode digital data, the sequence may be decoded to recover the digital data. Techniques for decoding digital data from the sequence output of a nucleotide sequencer are known to those of skill in the art (Church et al.; Organick et al.; Dimopoulou et al. 2020, ICASSP 2020).

If the particles 218 are to be discarded following storage, the particles may be degraded by placing them in a composting environment. A composting environment contains organic material such as food, leaves, wood, and dirt that are broken down by microorganisms. Anoxic composting environments also contain reducing agents that degrade the outermost layer 220 and the core 202 if it is also made of organosilicon disulfide. Oligonucleotides 200 will also degrade rapidly in a composting environment once the organosilicon disulfide encapsulation is removed.

Degradation of the particles 218 may also be achieved by use of a reducing agent such as TCEP to degrade the outermost layer 220 followed by destruction of the oligonucleotides 200. There are many known techniques for degrading oligonucleotides 200 once protective encapsulation is removed such as, but not limited to, addition of bleach.

Detail of procedures and techniques not explicitly described or other processes disclosed in this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, 4th ed. (2012).

EXAMPLES

Figure 3A:
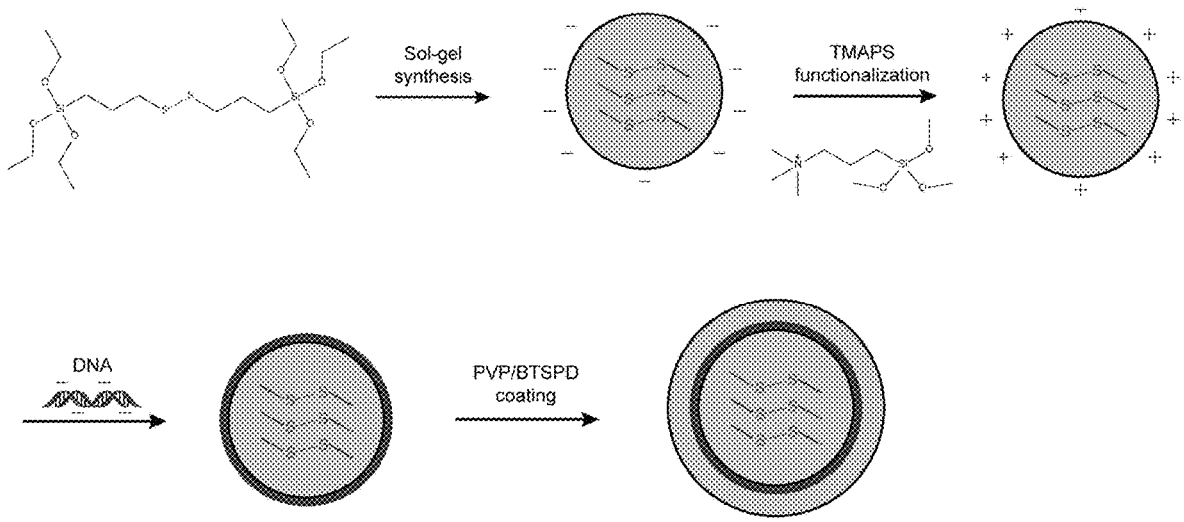
FIG. 3 shows a) a process for synthesizing particles according to techniques of this disclosure and b) a scanning transmission electron microscope (STEM) image of the particles. Scale bar is 1,000 nm.

FIG. 3a shows a schematic representation of the synthesis process described in the following examples. In brief, cores of hydrolyzed BTSPD are formed through sol-gel synthesis, the surface of the cores are functionalized with TMAPS to impart a positive surface charge, DNA is adsorbed to the cores through electrostatic attraction, the DNA is coated first with PVP and then a layer of hydrolyzed BTSPD is grown over the PVP-coated DNA.

All ultrapure water used in the examples was Milli-Q™ water (Millipore Corporation) with a purity such that resistivity is 18.2 MΩ·cm at 25° C. All Qubit measurements of DNA concentration were performed with Qubit™ dsDNA HS Assay Kit (ThermoFisher Scientific) and a Qubit™ fluorometer (ThermoFisher Scientific) according to manufacture instructions. All zeta potential and particle size measurements were performed with a Zetasizer Nano (Malvern) according to manufacture instructions.

Example 1: Particle Synthesis

The core synthesis was adapted from Croissant et al. Aspects of core synthesis not explicitly specified here are the same or similar to the technique provided in Croissant et al. Distilled water (100 ml), absolute ethanol (EtOH, 99.8%, 40 ml) and sodium hydroxide (NaOH, 2 M, 640 mg) were added to a two necked flask and stirred at 500 rpm. Next, cetyltrimethylammonium bromide (CTAB, 640 mg, 1.76 mmol) was added under stirring. The mixture was heated to 80° C. for 50 min under stirring (1000 rpm). After increasing the stirring speed to 1400 rpm, bis(3-triethoxysilylpropyl) disulfide (BTSPD, 2400 µl, 4.8 mmol) was added slowly. The resulting reaction mixture was stirred at 80° C. for 2 h. The mixture was then cooled to RT under stirring and the suspension distributed between four 50 ml Falcon® tubes (Fisher Scientific).

The cores were extracted twice with a solution of ammonium nitrate in ethanol ($NH_4NO_3$, 6 g/l, 20 ml) with sonication for 30 min at 50° C. and centrifugation for 15 minutes at 8000 g between each extraction. Next, the cores were washed with ethanol, then ultrapure water and once more with ethanol (each wash with 20 ml) before they were redispersed in ultrapure water and combined in one container for storage. The cores may be kept in storage indefinitely. The cores created by this synthesis are uniformly sized sub-micron particles. The zeta potential and the particle size were measured after completion of the synthesis at a core concentration of 0.1 g/l.

Figure 3B:
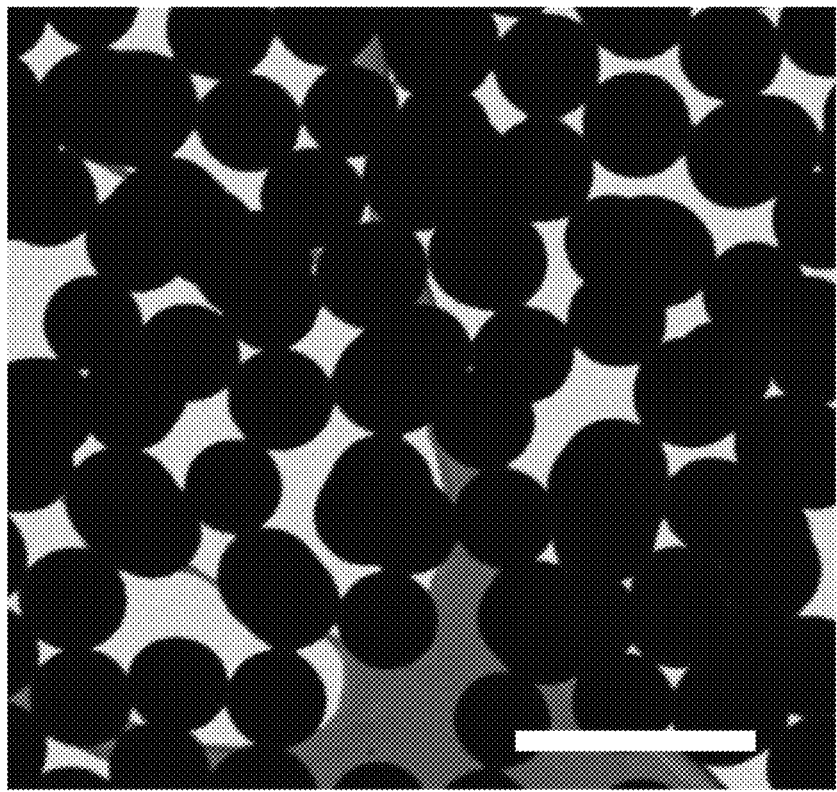
Figure 4A:
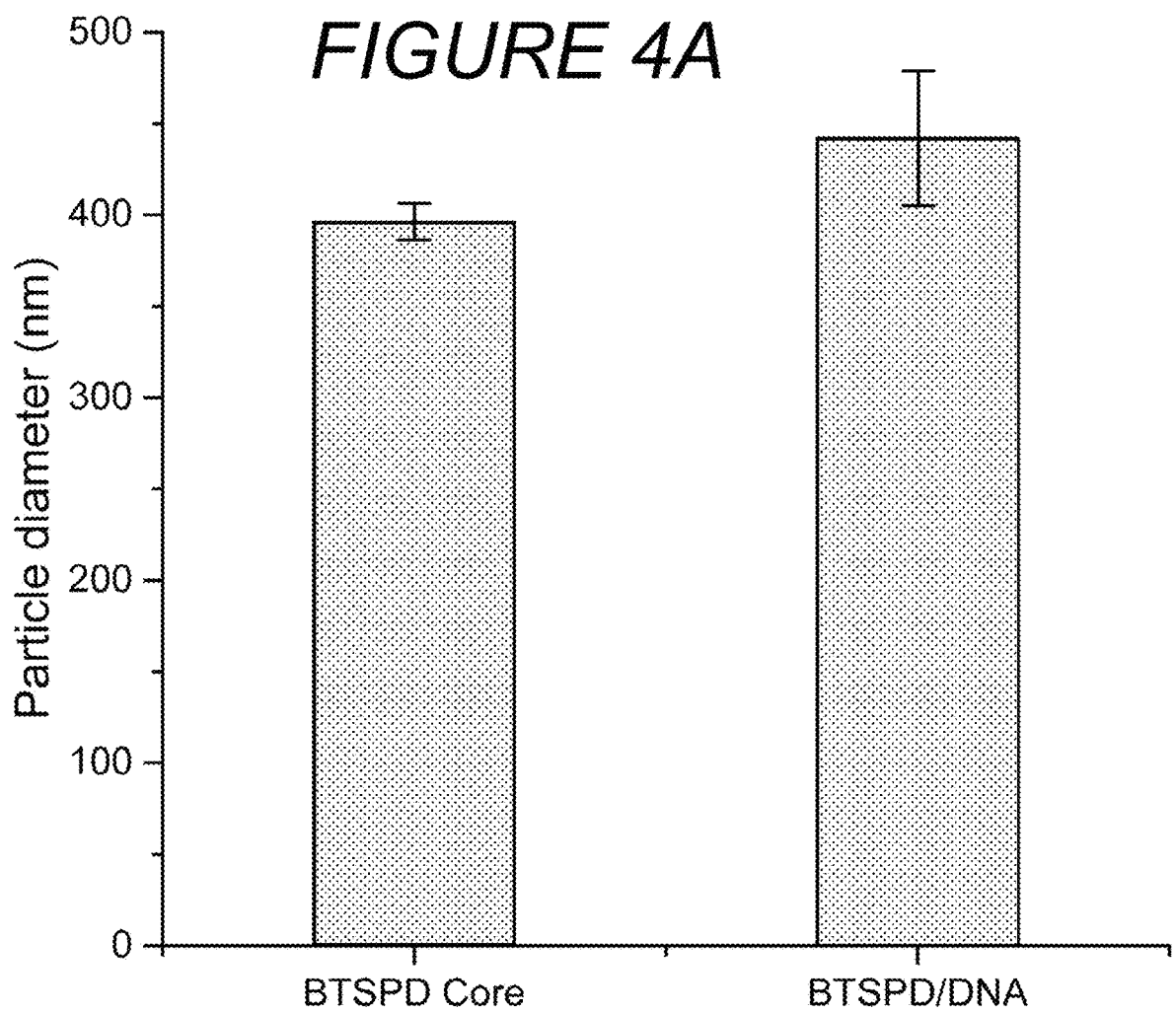
FIG. 4a compares the size of cores formed from the precursor bis(3-triethoxysilylpropyl) disulfide (BTSPD) to particles that include the cores coated with a DNA layer and encapsulated in an outer layer of hydrolyzed BTSPD.
Figure 4B:
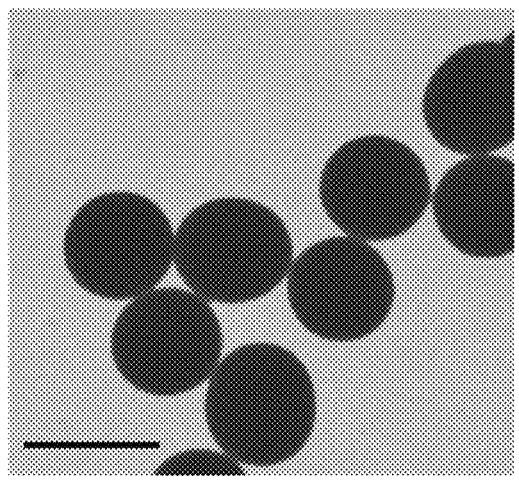
FIG. 4b is a STEM image of the hydrolyzed BTSPD cores. FIG.
Figure 4C:
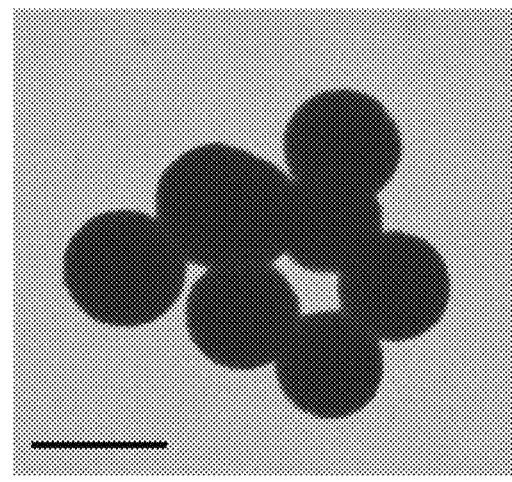

FIGS. 3b and 4b are STEM images of cores formed by this process suspended in ultrapure water. FIG. 3b shows images of the cores taken immediately after the synthesis. FIG. 4b shows cores from the same batch after 4-5 months of storage in water.

To functionalize the hydrolyzed BTSPD cores, TMAPS, a quaternary amine with a silyl moiety was reacted with the silyl on the core surface. The surface potential is thereby increased from −45.9 to +25.5 mV (measured by Zetasizer Nano). Next, 1 ml of hydrolyzed BTSPD core dispersion (50 mg/ml) in isopropanol (iPrOH, >99.5%) was prepared and thoroughly dispersed by sonication for about 10 min. To the dispersion, TMAPS (10 µl) was added. The mixture was stirred on a Thermoshaker (900 rpm for 12 h) and subsequently centrifuged (3 min at 21,500 g). The supernatant was removed, the cores were redispersed in iPrOH and the procedure repeated. Finally, the functionalized cores were suspended in iPrOH (1 ml, 50 g/l) for storage.

Double-stranded DNA (200 µl, 50 ng/µl, 65 nucleotides) was added to ultrapure water (800 µl) in an Eppendorf tube (2 ml), followed by the functionalized cores (35 µl, 50 mg/ml). After vortexing, the mixture was shaken for 20 min (500 rpm) and centrifuged (3 min, 15,000 g). The supernatant was removed and replaced with a PVP solution (750 µl, 45 g/l, molecular mass: 40 kg/mol). Without being bound by theory, it is believed that contacting that DNA with PVP produces a substrate that is more amenable for the growth of BTSPD than DNA alone. The DNA concentration of the supernatant was measured with a Qubit assay to determine the amount of DNA that was not adsorbed to the functionalized cores. In an earlier procedure, the DNA was shaken with the functionalized cores for only 3 minutes, but much of the DNA remained in the supernatant (data not shown). Thus, the shaking time was increased to 20 minutes; however, 20 minutes is not a hard threshold and shorter periods of shaking (e.g., 15, 16, 17, 18, or 19 minutes) will also produce adequate DNA absorption. With this technique, double-stranded DNA was successfully adsorbed on the surface of the TMAPS-functionalized core particles resulting in DNA-coated core particles containing 1.1% wt DNA.

To transfer the BTSPD/TMAPS/DNA particles from ultrapure water to EtOH, the particles were coated with PVP with an adapted synthesis route from Graf et al. 2003, Langmuir. Graf et al. describes coating with tetraethoxysilane (TES in Graf et al., also abbreviated TEOS) rather than BTSPD. Aspects of the process not explicitly described here may be assumed to be the same or similar to Graf et al.

Next, additional BTSPD was added to the PVP-coated particles in EtOH to grow a biodegradable layer of organosilicon disulfide coating. The particle suspension is vortexed and shaken for 24 hours (800 rpm), then centrifuged (100 rpm for 45 min). The supernatant is removed and replaced with 4.2% vol $NH_3$ in EtOH (1 ml). Ammonia is added to the suspension to increase the pH and accelerate the hydrolysis-polymerization. Without being bound by theory, it is believed that ammonia catalyzes the sol-gel polymerization of BTSPD. The particles are resuspended by vortexing and shaken at 900 rpm before adding BTSPD (1 µl). The suspension is left shaking for 2 days. The suspension is centrifuged for 3 min at 15,000 g and the supernatant removed. The particles are washed 2× with ultrapure water (500 µl). The particles are stored at 4-5° C. suspended in ultrapure water (500 µl).

FIG. 4a shows the growth in particle diameter following adsorption of the DNA and formation of the outer hydrolyzed BTSPD layer. The final particles, a biodegradable particle with encapsulated DNA (441±34 nm), increased in size 20-40 nm, as found by STEM image analysis. FIG. 4a is a STEM image of the cores before coating with DNA. FIG. 4b is a STEM image of the final particles.

Example 2: DNA Recovery

FIG. 5 shows the amount of DNA recovered from the particles created in Example 1. To release the DNA, the particles were suspended in Tris(2-carboxyethyl)phosphine (TCEP, 0.02M) or buffered oxide etch (BOE). BOE may be prepared by dissolving 0.23 g of ammonium hydrogen difluoride ($NH_4FHF$, puriss, Sigma-Aldrich, cat. no. 30101) in 5 mL of $H_2O$ and 0.19 g of $NH_4F$ (puriss, Sigma-Aldrich, cat. no. 30101) in 5 mL of $H_2O$ then mixing the two solutions together. TCEP is a reducing agent that breaks the sulfur-sulfur bonds in the BTSPD. BOE is a strong etching solution that breaks the silicon-oxygen bonds in the hydrolyzed BTSPD material. Both degrade the outer hydrolyzed BTSPD shell and core leaving the DNA in solution.

After 10 minutes incubation at room temperature, the solution was centrifuged (3 min, 15,000 g) and the supernatant collected and purified by QIAquick PCR purification kit. Ultrapure water was used as a negative control. The amount of DNA in the purified supernatant was measured by qPCR using standard protocols. Both TCEP and BOE provided similar and suitably high yields of DNA. The recovery of about 0.4 ng/μl represents approximately 0.3 wt % of DNA loading per mass of particles.

Example 3: Oxidative Challenge

The ability of the particles from Example 1 to protect DNA from oxidative damage was compared to other storage conditions by exposure to household bleach which creates oxidative conditions many times stronger than those experienced in standard storage conditions. A bleach stock was prepared with NaClO (14% activity, 8.57 ml), NaOH (10 M, 1.164 ml) and $H_2O$ (30.266 ml). 150-fold diluted bleach stock (143 μl) was added to pure DNA in ultrapure water ($10^{-4}$ ng/μl, 143 μl) as a positive control or to particles with encapsulated DNA (0.01 g/l, 143 μl) suspended in ultrapure water and incubated for 10 min. The reaction was then quenched by adding thiosulfate (1.46 M, 5 μl).

Figure 6A:
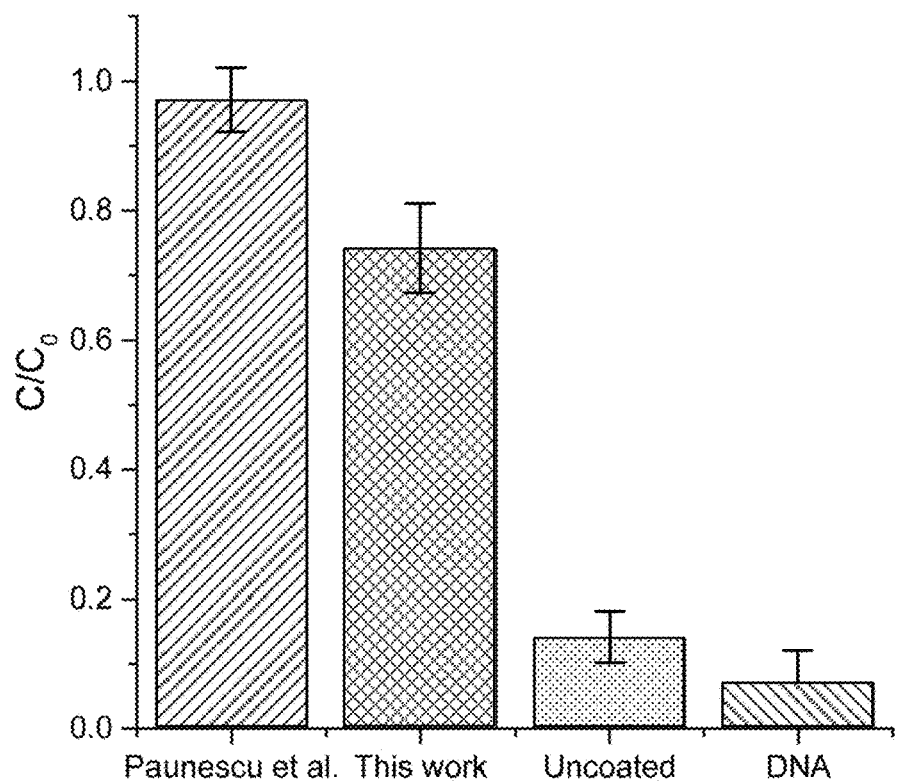

FIG. 6a is a bar chart that shows the change in the amount of DNA following oxidative challenge with bleach. The storage conditions tested were silica encapsulation as described in Paunescu et al. ("Paunescu et al."), the particles of Example 1 ("this work"), DNA adsorbed to a hydrolyzed BTSPD core without an outer coating ("uncoated"), and free DNA in solution ("DNA").

The DNA concentration was measured prior to oxidative challenge ($C_0$) and again after exposure to bleach (C). The volume of samples measured was the same at both time points. The ratio of $C/C_0$ indicates how much the concentration, or amount, of DNA changed following the oxidative challenge. Values less than 1 indicate a decrease in the amount of DNA. The concentration of unprotected DNA was directly measured by qPCR. For all the other storage conditions, the particles or cores were dissolved with BOE then the DNA was purified according to manufacture instructions with the QIAquick PCR purification kit (QIA-GEN) before qPCR quantification.

When treating encapsulated DNA, the recovery was higher than for non-encapsulated DNA. Particles synthesized according to Paunescu et al., showed 90% DNA recovery while particles synthesized in this work resulted in 70% DNA recovered. However, less than 20% of DNA was recovered when DNA was adsorbed on hydrolyzed BTSPD particles with no further coating and less than 10% of DNA was recovered, when simply dissolved in water. This indicates that both silica and BTSPD coatings protect encapsulated DNA from oxidative stress.

Example 4: Thermal Aging

Thermal aging simulates the damage caused by long-term storage at lower temperatures. Storage at 60° C. for 120 hours is believed to cause equivalent thermal damage as storage for 450 years at 10° C. or 5000 years at 0° C., assuming 1st order degradation kinetics with an activation energy of 155,000 J/mol. To test thermal aging, 15 Eppendorf tubes (2 ml) were each filled with either dialyzed DNA (15 ng/μl, 2 μl) or particles with encapsulated DNA (0.1 g/L, 5 μl). Using a vacuum centrifuge (45° C.), the open tubes were dried for 1 hour. Three tubes of each set were stored in a refrigerator (5° C.) while the rest were heat-treated with an open lid at 60° C. for up to 120 hours at 50% relative humidity. To each tube containing pure DNA, ultrapure water (100 μl) was added. An aliquot of the pure DNA in ultrapure water was further diluted 320× in additional ultrapure water. To each tube containing encapsulated particles, BOE (1:20, 100 μl) was added without further purification. All tubes were vortexed and then analyzed by qPCR.

Figure 6B:
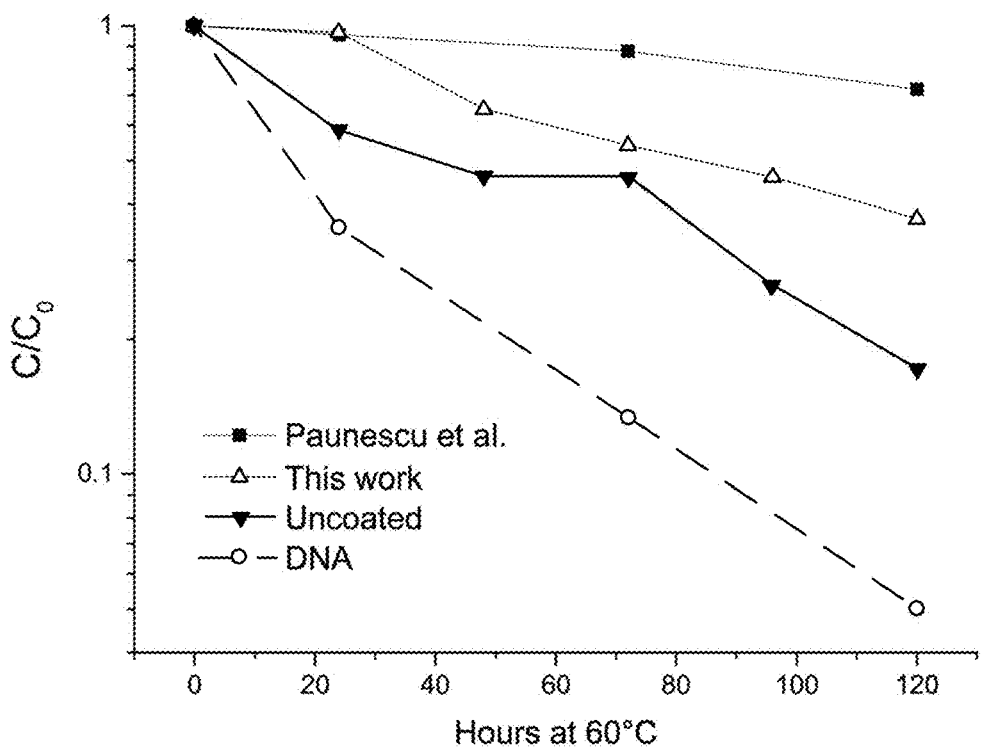

FIG. 6b is a line graph showing a decrease of DNA concentration while stored at 60° C. and 50% relative humidity. The storage conditions tested were silica encapsulation as described in Paunescu et al. ("Paunescu et al."), the particles of Example 1 ("this work"), DNA adsorbed to a BTSPD core without an outer coating ("uncoated"), and free DNA in solution ("DNA").

The DNA concentration was measured from the samples stored in the refrigerator ($C_0$) and at multiple time points during storage (C) at elevated temperature. The volume of samples measured was constant. The ratio of $C/C_0$ indicates how much the concentration, or amount, of DNA changed following exposure to elevated temperatures. Values less than 1 indicate a decrease in the amount of DNA. The results show that silica and hydrolyzed BTSPD encapsulation stabilize DNA compared to adsorption on uncoated cores or being free in solution.

Example 5: Degradability with Chemical Reducing Agents

Degradability of the particles from Example 1 was tested by exposure to two different chemical reducing agents. First, the particles were exposed to reducing conditions reflecting a typical intracellular reducing environment in a biological cell. A solution of glutathione (GSH, 8 mM) at pH 7.2 was prepared. The solution was degassed by bubbling $N_2$. The particles (80 μg/ml) were added to Eppendorf tubes, sealed airtight, and incubated at 37° C. and 18 rpm shaking for 30 days.

FIG. 7a shows scanning transmission electron microscopy (STEM) images of the particles demonstrating a visible decrease in particle size during 30 days of exposure to GSH. The diameter of the particles decreased to around 150 nm at day 30 compared to approx. 370 nm at day 0. This gradual decrease in particle size indicates the techniques described in Example 1 create a solid, hydrolyzed BTSPD outer layer. Porous, hydrolyzed BTSPD would degrade faster under these reducing conditions.

Next, the core particles of Example 1 were subjected to TCEP (0.2 M) to test the degradation of the hydrolyzed BTSPD core particle. TCEP is a reducing agent commonly used in biochemical and molecular biology applications. TCEP is a stronger reducing agent than GSH.

FIG. 7b shows the particles in water before the addition of TCEP and following the addition of TCEP. The particles completely dissociated shortly (i.e., within minutes) after the addition of TCEP as confirmed visibly by eye and by STEM imaging.

Example 6: Biodegradability in Composting Conditions

Biodegradability in composting conditions was tested by placing particles in a laboratory-scale air-tight and wetted composting environment as defined in ISO 20200:2015. Anaerobic composting environments produce reducing conditions with redox potentials from −300 to −100 mV (Nghiem et al. Biores. Tech., 2014; Reddy & Patrick, Soil Biol. Biochem. 1974) as oxygen is used up and organic material decomposes. The reducing conditions in the composting environment tested are believed to be at least as strong as those produced by exposure to GSH in Example 5.

FIG. 8 is a line graph showing a decrease in DNA concentration over time while in a composting environment. "Paunescu et al." are silica encapsulated particles produced according to the techniques of Paunescu et al. "This work" represents the particles with hydrolyzed BTSPD encapsulation produced as described in Example 1. Particles were mixed with the compost to a final concentration of 50 ppm. DNA represents "naked" DNA in a buffer solution and is the same as used for encapsulation in Example 1. The DNA was mixed with the compost to a final concentration of 0.25 ppm. The DNA concentration was measured from the samples stored in the freezer (−20° C.) ($C_0$) and at multiple time points during storage (C) in the composting environment at 40° C. To extract DNA from compost samples, 100 µg compost was mixed with 100 µl BOE and 200 µl ultrapure water. After mixing, the solid residues were centrifuged (3 min, 15,000 g) while the supernatant was purified with QIAquick PCR purification kit. The ratio of $C/C_0$ indicates how much the concentration, or amount, of DNA changed following exposure to composting environment. This shows that silica encapsulation ("Paunescu et al.") provides strong protection that does not degrade in composting environments. However, particles formed of hydrolyzed BTSPD ("this work") degrade in composting environments exhibiting a decrease in DNA concentration similar to unprotected DNA.

These examples demonstrate an encapsulation strategy, which protects DNA from chemical and hydrological stress, but is degradable in reducing conditions as expected in compost and biological systems.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A particle comprising: a positively charged core; an oligonucleotide layer adsorbed to the positively charged core; an interacting layer comprising polyvinylpyrrolidone (PVP) adsorbed to the oligonucleotide layer; and an outermost layer of non-porous, hydrolyzed organosilicon disulfide.

Clause 2. The particle of clause 1, wherein the positively charged core has a diameter of between 100 and 500 nm.

Clause 3. The particle of clause 1-2, wherein the positively charged core is functionalized with amine groups.

Clause 4. The particle of clause 1-3, wherein the positively charged core comprises silica, mesoporous silica, or hydrolyzed organosilicon disulfide.

Clause 5. The particle of clause 1-4, wherein the positively charged core is porous or non-porous.

Clause 6. The particle of clause 1-5, wherein the outermost layer of non-porous, hydrolyzed organosilicon disulfide comprises a hydrolyzed disulfide triethoxysilane.

Clause 7. The particle of clause 6, wherein the hydrolyzed disulfide triethoxysilane is hydrolyzed bis(3-triethoxysilylpropyl) disulfide (BTSPD).

Clause 8. The particle of clause 1-7, wherein core comprises hydrolyzed BTSPD and the outermost layer of non-porous, hydrolyzed organosilicon disulfide comprises hydrolyzed BTSPD.

Clause 9. The particle of any of clauses 1-8, further comprising: a positively charged layer containing a polycationic molecule adsorbed to the oligonucleotide layer; and a second oligonucleotide layer adsorbed to the positively charged layer.

Clause 10. A method for creating a particle comprising: functionalizing a core to create a positively charge on the core; contacting the core with oligonucleotides; contacting the core with polyvinylpyrrolidone (PVP); and encapsulating the core in an organosilicon disulfide.

Clause 11. The method of clause 10, wherein the core comprises silica, mesoporous silica, or hydrolyzed organosilicon disulfide.

Clause 12. The method of clause 10-11, further comprising synthesizing the core by a sol-gel process.

Clause 13. The method of clause 10-12, wherein the functionalizing the core comprises contacting the core with an amino silane.

Clause 14. The method of clause 10-13, wherein contacting the core with the oligonucleotides comprises shaking the core with the oligonucleotides for about 20 minutes.

Clause 15. The method of clause 10-14, wherein the hydrolyzed organosilicon disulfide comprises a hydrolyzed disulfide triethoxysilane.

Clause 16. The method of clause 15, wherein the hydrolyzed disulfide triethoxysilane is bis(3-triethoxysilylpropyl) disulfide (BTSPD).

Clause 17. The method of clause 10-16, wherein encapsulating the core in the hydrolyzed organosilicon disulfide comprises adding organosilicon disulfide precursor to the core while shaking in a solution of ammonia in ethanol for at least about 24 hours.

Clause 18. The method of clause 10-17, further comprising contacting the oligonucleotides with polycationic molecules and contacting the polycationic molecules with second oligonucleotides to create a second layer of oligonucleotides separated by the polycationic molecules from the oligonucleotides.

Clause 19. The method of clause 10-18, further comprising releasing the oligonucleotides by contacting the particle with a reducing agent.

Clause 20. The method of clause 10-19, further comprising degrading the particle including the oligonucleotides by placing the particle in a composting environment.

Clause 21. A particle formed by the method of any of clauses 10-20.

Clause 22. A method to store digital data comprising: encoding digital data in a nucleotide sequence; synthesizing oligonucleotides having at least a portion of the nucleotide sequence; and creating a particle according to any of clauses 1-9, wherein the oligonucleotide layer comprises the oligonucleotides.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for its particular cited teachings as well as for all that it discloses.

The invention claimed is:

1. A particle comprising:
a porous, positively charged core comprising a blend of bis(triethoxysilyl)ethylene and bis(3-triethoxysilylpropyl) disulfide (BTSPD);
an oligonucleotide layer adsorbed to the positive charged core;
an interacting layer comprising polyvinylpyrrolidone (PVP) adsorbed to the oligonucleotide layer; and
an outermost layer of non-porous, hydrolyzed organosilicon disulfide, wherein a diameter of the particle is about 440 nm.

2. The particle of claim 1, wherein the positively charged core has a diameter of at least 100 nm.

3. The particle of claim 1, wherein the positively charged core is functionalized with amine groups.

4. The particle of claim 1, wherein the outermost layer of non-porous, hydrolyzed organosilicon disulfide comprises a hydrolyzed disulfide triethoxysilane.

5. The particle of claim 4, wherein the hydrolyzed disulfide triethoxysilane is hydrolyzed bis(3-triethoxysilylpropyl) disulfide (BTSPD).

6. The particle of claim 1, wherein the positively charged core comprises hydrolyzed BTSPD and the outermost layer of non-porous, hydrolyzed organosilicon disulfide comprises hydrolyzed BTSPD.

7. The particle of claim 1, further comprising:
a positively charged layer containing a polycationic molecule adsorbed to the oligonucleotide layer; and
a second oligonucleotide layer adsorbed to the positively charged layer.

8. A particle comprising:
a porous, positively charged core comprising a blend of bis(triethoxysilyl)ethylene and hydrolyzed bis(3-triethoxysilylpropyl) disulfide (BTSPD);
an oligonucleotide layer adsorbed to the positively charged core;
a positively charged layer containing a polycationic molecule adsorbed to the oligonucleotide layer; and
a second oligonucleotide layer adsorbed to the positively charged layer;
an interacting layer comprising polyvinylpyrrolidone (PVP) adsorbed to the second oligonucleotide layer; and
an outermost layer of non-porous, hydrolyzed organosilicon disulfide comprising BTSPD, wherein a diameter of the particle is about 440 nm.

9. The particle of claim 8, wherein the positively charged core has a diameter of at least 100 nm.

10. The particle of claim 8, wherein the positively charged core is functionalized with amine groups.

11. The particle of claim 8, wherein the positively charged core comprises silica.

12. The particle of claim 8, wherein the outermost layer of non-porous, hydrolyzed organosilicon disulfide comprises a hydrolyzed disulfide triethoxysilane.

13. The particle of claim 12, wherein the hydrolyzed disulfide triethoxysilane is hydrolyzed bis(3-triethoxysilylpropyl) disulfide (BTSPD).

14. The particle of claim 8, further comprising:
a second positively charged layer containing a polycationic molecule adsorbed to the oligonucleotide layer; and
a third oligonucleotide layer adsorbed to the positively charged layer.

15. A method for creating a particle comprising:
functionalizing a porous, positively charged core comprising a blend of bis(triethoxysilyl)ethylene and bis(3-triethoxysilylpropyl) disulfide (BTSPD) to create a positive charge on the core;
contacting the core with oligonucleotides;
contacting the core with polyvinylpyrrolidone (PVP); and encapsulating the core in non-porous, hydrolyzed organosilicon disulfide such that the particle created has a diameter of about 440 nm.

16. The method of claim 15, further comprising synthesizing the core by a sol-gel process.

17. The method of claim 15, wherein the functionalizing the core comprises contacting the core with an amino silane.

18. The method of claim 15, wherein contacting the core with the oligonucleotides comprises shaking the core with the oligonucleotides for about 20 minutes.

19. The method of claim 15, wherein the hydrolyzed organosilicon disulfide comprises a hydrolyzed disulfide triethoxysilane.

20. The method of claim 15, further comprising contacting the oligonucleotides with polycationic molecules and contacting the polycationic molecules with second oligonucleotides to create a second layer of oligonucleotides separated by the polycationic molecules from the oligonucleotides.

* * * * *